United States Patent [19]

Hillhouse

[11] Patent Number: 5,550,295
[45] Date of Patent: Aug. 27, 1996

[54] PREPARATION OF ARYLALKYL PHOSPHINES, PHOSPHINE OXIDES OR PHOSPHINE SULFIDES

[75] Inventor: John H. Hillhouse, Niagara Falls, Canada

[73] Assignee: Cytec Technology Corp., Wilmington, Del.

[21] Appl. No.: 433,612

[22] Filed: May 3, 1995

[51] Int. Cl.⁶ ........................................................ C07F 9/02
[52] U.S. Cl. ................................................. 568/14; 568/17
[58] Field of Search ........................................ 568/14, 17

[56] References Cited

U.S. PATENT DOCUMENTS

| | | | |
|---|---|---|---|
| 3,775,482 | 11/1973 | Hewertson et al. | 260/606.5 P |
| 4,618,720 | 10/1986 | Bay et al. | 568/17 |
| 4,668,823 | 5/1987 | Murray | 568/17 |
| 5,288,912 | 2/1994 | Devon | 568/17 |
| 5,354,894 | 10/1994 | Devon | 568/17 |

OTHER PUBLICATIONS

Organic Chemistry, vol. 57, pp. 3558–3563, 1992.
Synthesis, Mar. 1991, pp. 232 and 233, Loffler et al; Mar. 1986 pp. 240–242, Xu et al; and Mar. 1986 pp. 691–692.
Tetrahedron Letters, vol. 35; No. 24; pp. 4133–4136, 1994.

*Primary Examiner*—Porfirio Nazario-Gonzales
*Attorney, Agent, or Firm*—Frank M. Van Riet

[57] ABSTRACT

Arylalkyl phosphines, phosphine oxides or phosphine sulfides are prepared by reacting an alkyl phosphine, phosphine oxide or phosphine sulfide with an arylhalide in the presence of a zero valence palladium catalyst.

11 Claims, No Drawings

PREPARATION OF ARYLALKYL PHOSPHINES, PHOSPHINE OXIDES OR PHOSPHINE SULFIDES

BACKGROUND OF THE INVENTION

This invention relates to an improved process for the production of arylakyl phosphines, phosphine oxides and phosphine sulfides. The process comprises the reaction of an alkyl phosphine, phosphine oxide or phosphine sulfide with an arylhalide in the presence of a zero valence palladium catalyst. This process has the advantages of fast reaction rates at relatively low temperature, avoidance of phosphine halides and Grignard reagents and a relatively simplified work-up of reactants.

The preparation of arylalkyl phosphines, phosphine oxides and phosphine sulfides is known in the art. However, previous processes for the preparation of these compounds involve the use of reagents which are either cumbersome to work with or entail the need for detailed work-ups and extraordinary production conditions and precautions.

U.S. Pat. No. 3,775,482, for example, disclose the use of alkali metal whereby tetrahydrocarbyl diphosphines are reacted therewith in a solvent such as tetrahydrofuran and the resultant phosphide is isolated. A fused ring polynuclear aromatic hydrocarbon or diphenyl is used as a catalyst.

U.S. Pat. No. 4,618,720 discloses a two-step process whereby a diphenylphosphinous halide is reacted with a molten alkali metal in the presence of an inert solvent and the resultant diphenylphosphinous metal is then reacted with a second halide wherein an excess of molten alkali metal is employed and the second halide is added in situ.

U.S. Pat. No. 4,668,823 teaches the production of alkylarylphosphines by the sequential addition of different Grignard reagents to aryldichlorophosphines. The first Grignard reagent having an alkyl group is reacted with an aryldichlorophosphine and the resultant arylalkylchlorophosphine is reacted with the second Grignard reagent having a different alkyl or aryl groups.

U.S. Pat. No. 5,288,912, and its divisional counterpart U.S. Pat. No. 5,354,894, teach the preparation of alkyldiarylphosphine compounds by the reaction of alkali metal diarylphosphides with alkylhalide alkylating agents via lithium cleavage.

Cabri et al, J. Org. Chem. Vol. 57, pgs. 355–3563, 1992, teach the arylation of unsymmetrical olefins using bidentate phosphine containing palladium catalysts.

Ono et al, Tetrahedron Letters, Vol. 35, No. 24, pages 4133–4136, 1994 report on the arylation of N-alkyI-O-allyl carbamates using a palladium catalyst.

In Synthesis, March 1991, pages 232 and 233, Loffler et al report on the coupling of (1,3 -butadiynyl) amines with aryl and vinyl iodides using a palladium catalyst and in March 1986, pages 240–242, Xu et al teach the use of palladium catalysts to synthesize alkyl alkenylmethyl and alkenylphenylphosphinates followed by a report in March 1986, pages 691–692 of the preparation of corresponding phosphine oxides with the same catalyst system.

SUMMARY OF THE INVENTION

There is disclosed herein a process for the preparation of arylalkylphosphines, phosphine oxides and phosphine sulfides, including diarylalkyl and dialkylaryl derivatives. The process comprises the reaction of a mono or dialkyl phosphine, phosphine oxide or phosphine sulfide with an aryl halide in the presence of a zero valence palladium catalyst. The products of the reaction may be used as promotors in the hydroformylation of olefins to aldehydes using rhodium-based catalysts, as intermediates in the production of additional phosphine-based chemicals such as those useful as extractants, detergents, flame-proofing agents, biocides etc. and as catalyst ligands.

DESCRIPTION OF THE INVENTION INCLUDING PREFERRED EMBODIMENTS

The instant invention comprises a process for the production of a compound having the formula:

wherein X is oxygen or sulfur, n is 0 or 1, Ar is a substituted or unsubstituted aryl radical, R is a substituted or unsubstituted alkyl radical, x is 0 or 1 and y and z are 1 or 2, with the proviso that when x is 0, only one of y and z is 2 and when x is 1, both of y and z are 1, which comprises reacting a compound having the formula

wherein X, n, R and z are as defined above, with an arylhalide in the presence of a zero valence palladium catalyst.

The reaction is preferably carried out in the presence of a solvent such as glyme, acetonitrile, diethyl ether, anisole, di-n-butyl ether, tetrahydrofuran, p-dioxane, tolene/isopropanol (3/1) mixtures and the like. Aliphatic, cyoloalphatic or aromatic hydrocarbons are preferred including hexane, octane, cyclohexane, benzene and 70°–140° C. petroleum boiling fractions. Toluene is most preferred.

The temperature of the reaction can range from about ambient to about 120° C., preferably from about 40°–110° C. and most preferably from about 70 –105° C. At lower temperatures, the time of reaction is increased however, the reaction is usually complete within from about 2 hours to about 2 weeks, more usually in from about 3 to about 36 hours.

The zero valence palladium catalysts useful in the instance process are well known to those skilled in the art and any such known catalyst may be used i.e. those catalysts which are reduced in situ to the Pd(o) species under the conditions of the reaction. Specifically those taught in the above cited references may be used herein, with such catalysts as tetrakis (triphenylphosphine) palladium; dichlorobis (triphenylphosphine) palladium; 1,2-bis(diphenylphosphino) ethane palladium; 1,3-bis(diphenylphosphino) propane palladium; 1,4-bis(diphenylphosphino) butane palladium; 1,1-bis(diphenylphosphino) ferrocene palladium etc. being exemplary. The catalyst concentration should range from about 0.1 to about 10.0 mole percent of the charge phosphine of Formula II, above, preferably from about 1.0 to about 7.5 mole percent.

The reaction is preferably carried out in the presence of a base promotor such as an amine e.g. triethylamine, potassium carbonate, cesium carbonate, sodium bicarbonate, potassium bicarbonate, sodium ethoxide, potassium ethoxide, ammonium carbonate, ammonium bicarbonate, calcium oxide, calcium hydroxide, magnesium oxide, magnesium hydroxide and the like. Additionally, bases such as pyridine and pyridine derivatives may also be used. Tertiary amines are preferred and triethylamine is most preferred.

In the charge phosphines, phosphine oxides and phosphine sulfides of Formula II, above, the alkyl radical R may be substituted or unsubstituted and may contain one to 20 carbon atoms. Primary, secondary and tertiary alkyl, cycloalkyl and bicycloalkyl group-containing phosphines, phosphine oxides and phosphine sulfides are useful in the present invention including methyl, ethyl, propyl, n-,t- or isobutyl, pentyl, hexyl, heptyl, octyl, nonyl, decyl, undicyl, hexadicyl, cyclohexyl cyclopentyl, etc. groups and aryl, alkenyl, alkoxy, alkanyl, halo, aryloxy etc. substituted derivatives thereof.

The arylhalides include those aryl compounds wherein the aryl group contains from 6–10 carbon atoms, e.g., the arylchlorides, bromides, iodides etc. as represented by chlorobenzene, bromobenzene, iodobenzene, chlorotoluene, chloroxylene, chloronaphthalene, bromonaphthalene, iodonaphthalene, chlorodiphenyl, bromotoluene, bromoxylene, bromodiphenyl, iodotoluene, iodoxylene, iododiphenyl and alkyl, alkenyl, alkoxy, alkaryl, aryloxy etc. substituted derivatives thereof.

The amount of arylhalide employed should constitute an equivalent excess of arylhalide to the dialkylphosphine, phosphine oxide or phosphine sulfide employed e.g. approximately 1.1 equivalents of arylhalide. When a monoalkyl phosphine, phosphine oxide or phosphine sulfide is employed, an excess of two equivalents of the aryl halide should be used e.g. 2.1 equivalents.

The amount of the base promoter used should be within the above amounts taught for the arylhalides and preferably the amount of base promotor and arylhalide used during each reaction is about the same.

Alternatively, the reaction can be governed by the temperature of the reaction and the reaction with the alkylhalide can be terminated without complete hydrogen replacement of the charge compound (11) such as by cooling to below ambient temperature, or by use of a polar cosolvent such as isopropyl alcohol in 5–25% proportion. The resultant intermediate may be recovered such as by distallation from the crude mixture.

The final reaction products corresponding to Formula (I) may be analyzed by gas chromatography—mass spectrometry to determine their ultimate structure, with products identified from their mass spectrum (usually containing a parent ion corresponding to the molecular weight of the product).

The following examples ar set forth for purposes of illustration only and are not to be construed as limitations on the present invention except as set forth in the appended claims. All parts and percentages are by weight unless otherwise specified.

EXAMPLE 1

A mixture of diisobutylphosphine, (50 g, 0.34 mole), bromobenzene (54 g, 0.34 mole), triethylamine (36 g, 0.35 mole) tetrakis (triphenylphosphine) palladium (1.0 g, 8.6×10−5 mole) in toluene (100 mL) is heated to 100° C. under nitrogen and maintained at this temperature for 13 hours. After cooling to room temperature the solution is analyzed by GC/MS and found to contain 94% diisobutyl (phenyl)phosphine (mw–222) along with approximately 6% unreacted diisobutylphosphine (mw=196). The triethylamine hydrobromide byproduct is removed by filtration. The mixed diisobutylphenyl phosphine product is isolated from the mixture by vacuum distillation.

EXAMPLE 2

The mixed diisobutylphenyl phosphine product of Example 1 is converted to the corresponding derivative with aqueous hydrogen peroxide to prepare diisobutylphenyl phosphine oxide.

EXAMPLE 3

A mixture of bis(2,4,4-trimethylpentyl)phosphine oxide (2.3 g, 8.4×10−3 mole), bromobenzene (1.3 g, 8.3×10−3 mole), triethylamine (2.0 g, 2.0×10−2 mole) and tetrakis (triphenylphosphine)palladium (1.0 g, 8.5×10−4 mole) in toluene (15 mL) is heated to 85° C. under nitrogen. This mixture is maintained at this temperature for four hours, then allowed to cool to room temperature. Analysis of the mixture at this time by GC/MS indicates complete (>99%) conversion of the dialkylphosphine oxide to bis (2,4,4-trimethylpentyl)phenylphosphine (mw=334). The mixed diisobutylphenyl converted to the corresponding derivative with aqueous hydrogen peroxide to prepare the diisobutylphenyl phosphine oxide.

EXAMPLE 4

A mixture of monoisobutylphosphine (2.0 g, 0.022 mole), iodobenzene (10.0 g, 0.049 mole), triethylamine (5.5 g, 0.054 mole) and tetrakis(triphenylphosphine) palladium ( 1.0 g, 8.6×10−4 mole) in toluene (30 mL) is heated to 70° C. under nitrogen. The mixture is maintained at 70° C. with magnetic stirring for four hours. At this time the mixture is allowed to cool to ambient temperature. Analysis of the mixture by GC/MS indicates 95% conversion of monisobutylphosphine to di (phenyl) isobutylphosphine (mw=242).

EXAMPLE 5

A mixture of bis(2,4,4-trimethylpentyl)phosphine sulphide (3.0 g, 0.010 mole), bromobenzene (2.0 g, 0.013 mole), triethylphosphine (2.0 g, 0.020 mole) and tetrakis(triphenylphosphine)palladium (1.0 g, 8.6×10−4 mole) in toluene (15 mL) is heated to 70° C. for approximately 30 hours. At this time analysis of the mixture indicates that approximately 42% conversion of the dialkylphosphine sulphide to bis(2,4,4-trimethylpentyl)phenylphosphine sulphide (mw=336) has occurred.

EXAMPLE 6

A mixture of 2,4,6-triisopropyl-1,3-dioxa-5-phosphacyclohexane (5.6 g, 0.025 mole), bromobenzene (4.0 g, 0.026 mole), triethylamine (2.8 g, 0.028 mole) and tetrakis(triphenylphosphine)palladium (1.0 g, 8.6×10−4 mole) is heated to 75° C. under nitrogen and maintained at this temperature for 24 hours. Analysis of the mixture by GC/MS indicates that >90% of the starting cyclic dialkylphosphine has been converted to the 2,4,6-triisopropryl-1,3-dioxa-5-phenyl-5-phosphacyclohexane. After oxidation of the crude mixture with hydrogen peroxide and purification by recrystallization, the final diakylmonoaryl phosphine oxide product is fully characterized (mp 915°–198° C., $^{31}$P NMR, singlet+12.6 ram; EI mass spectrum, parent m/z at 324 amu).

EXAMPLE 7

A mixture of diisobutylphosphine (4.5 g, 0.031 mole), 1-bromonaphthalene (6.5 g, 0.031 mole), triethylamine (3.5 g, 0.035 mole) and tetrakis(triphenyphosphine)palladium (1.0 g) in toluene (100 mL) is heated to 75° C. under nitrogen, and maintained at this temperature for 10 hours. Analysis of the mixture at this time by GC/MS indicates >90% conversion of diisobutylphosphine to 1-diisobutylphosphinonaphthalene (mw=272).

EXAMPLE 8

A mixture of diisobutylphosphine (75 g, 0.51 mole), 4-bromotoluene (89 g, 0.52 mole), triethylamine (55 g, 0.54 mole), tetrakis (triphenylphosphine)palladium (1.0 g, 8.6× $10^{-4}$ mole) in toluene (150 mL) is heated to 100° under nitrogen with mechanical agitation. The mixture is maintained at this temperature for 24 hours, the cooled to room temperature. Analysis of this mixture by GC/MS indicates approximately 85% conversion of diisobutyl-phosphine to diisobutyl(p-tolyl)phosphine, with no other byproducts observed.

EXAMPLE 9

A mixture of monoisobutylphosphine (2.0 g, 0.22 mole), iodobenzene (9.5 g, 0.47 mole), triethylamine (5.0 g, 0.049 mole), tetrakis (triphenylphosphine)palladium (1.0 g, 8.5× $10^{-4}$ mole) in toluene (30 mL) containing approximately 5% (v/v) isopropyl alcohol is maintained at 70° C. under nitrogen for four hours. At this time anaylsis of the mixture by GC/MS indicates a 1:1 mixture of isobutyl(phenyl)phosphine and isobutyl di(phenyl) phosphine, with no sign of any remaining monoisobutyl phosphine starting material. Further heating of this mixture at 70° C. results in complete conversion of the intermediate isobuty(phenyl)phosphine to isobutyl di(phenyl)phosphine after approximately six hours.

We claim:

1. A process for the preparation of a compound having the formula

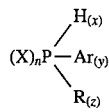

wherein X is O or S, n is 0 or 1; Ar is a substituted or unsubstituted aryl radical, R is a substituted or unsubstituted alkyl radical, x is 0 or 1 and y and z are 1 or 2, with the proviso that when x is 0, only one of y and z is 2 and when x is 1, both of y and z are 1, which comprises reacting a compound having the formula:

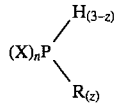

wherein X, n, R and z are as defined above, with an arylhalide in the presence of a zero valence palladium catalyst.

2. A process according to claim 1 wherein R is 2,4,4-trimethylpentyl.

3. A process according to claim 1 wherin Ar is phenyl.

4. A process according to claim 2 wherein Ar is phenyl.

5. A process according to claim 1 wherein R is isobutyl.

6. A process according to claim 5 wherein Ar is phenyl.

7. A process according to claim 1 wherein an amine base promoter is present during the reaction.

8. A process according to claim 1 wherein the catalyst is tetrakis palladium.

9. A process according to claim 1 wherein z is 2.

10. A process according to claim 1 wherein Y is 2.

11. A process according to claim 7 wherein the promotor is triethylamine.

* * * * *